United States Patent
Taylor (10) Patent No.: US 8,372,077 B2
(45) Date of Patent: Feb. 12, 2013

(54) SAW FOR THE REMOVAL OF A PROSTHESIS

(75) Inventor: Andrew Clive Taylor, West Sussex (GB)

(73) Assignee: Finsbury (Development) Limited, Leatherhead (GB)

( * ) Notice: Subject to any disclaimer, the term of this patent is extended or adjusted under 35 U.S.C. 154(b) by 336 days.

(21) Appl. No.: 12/263,135

(22) Filed: Oct. 31, 2008

(65) Prior Publication Data

US 2010/0069909 A1    Mar. 18, 2010

(30) Foreign Application Priority Data

Oct. 31, 2007    (GB) .................................. 0721386.1

(51) Int. Cl.
*A61B 17/00*    (2006.01)
(52) U.S. Cl. ................. 606/82; 606/83; 606/99
(58) Field of Classification Search ............ 606/82, 606/86 R, 176–184; 83/835; 28/260; 30/130–139; D08/95
See application file for complete search history.

(56) References Cited

U.S. PATENT DOCUMENTS

| 5,382,251 A | 1/1995 | Hood et al. |
| 2007/0123893 A1* | 5/2007 | O'Donoghue ................. 606/82 |

FOREIGN PATENT DOCUMENTS

| WO | 8805645 | 8/1988 |
| WO | 2006059120 | 6/2006 |
| WO | WO 2006059120 A1 * | 6/2006 |

* cited by examiner

*Primary Examiner* — Andrew Yang
*Assistant Examiner* — Olivia C Chang
(74) *Attorney, Agent, or Firm* — Armstrong Teasdale LLP (57) ABSTRACT

In a saw for the removal of a prosthesis which is integrated with a bone, a blade is connected to a handle wherein the distal end of the blade includes a shaped nib. The shaped nib has teeth, with at least some of the teeth being angled to cut as the saw is moved in a backward direction. The nib additionally includes means for allowing the nib to be reversibly deformed such that in use its maximum width can be temporarily reduced.

13 Claims, 9 Drawing Sheets

SAW FOR THE REMOVAL OF A PROSTHESIS

FIELD OF THE INVENTION

The present invention relates to a tool for removing a prosthesis integrated with a bone. More particularly, it relates to a tool for removing a femoral head prosthesis implanted in the femur of a patient.

The skeletal and muscular structure of the human body is complex. In particular, the joints between bones which enable the body to articulate can be very complex. Unfortunately, due to defects present at birth, damage caused through injury, and/or wear or deposition which occurs with age, these joints may not function satisfactorily. Joint problems may reduce the mobility, flexibility or, where the joints are in the hand, the dexterity, of the patient, and thus prostheses have been suggested which can be inserted to replace all or a part of the natural joint. The shape of a particular joint prosthesis will depend on the joint, or part thereof, which is to be replaced. However, the prosthesis will generally include a shaft, pin or the like which is implanted into the bone to enable the prosthetic joint, or part thereof, to be located securely in the correct position and orientation.

In particular, it will be acknowledged that the efficient functioning of the hip joints is extremely important to the well being and mobility of the human body. Each hip joint is comprised by the upper portion of the femur which terminates in an offset bony neck surmounted by a ball-headed portion, known as the femoral head. This femoral head rotates within a socket, known as the acetabulum, in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming misshapen. This misshapen joint may cause pain and may eventually cease to function altogether.

Operations to replace the hip joint, or one component thereof, with an artificial implant are well-known and widely practiced. Generally, the hip prosthesis will be formed of two components, namely: an acetabular, or socket, component which lines the acetabulum; and a femoral, or stem, component which replaces the femoral head. In order to insert the femoral component into the patient's femur, the surgeon must remove the femoral head and then hollow out the upper portion of the femur using reamers and rasps so that the stem of the prosthesis can be inserted.

Although the stem is generally a tight fit in the bone, bone cement is generally used to hold the stem portion of the femoral prosthesis in position. Additionally, or alternatively, the stem may be held in place by bone in-growth and in some arrangements, the stem of the prosthesis may be coated with material, such as hydroxyapetite, to promote the bone in-growth. Bone in-growth is where the natural bone knits with the prosthesis. Thus, the bone and the prosthesis become integrated. The combination of the cement and the bone in-growth means that after an initial settlement period, the prosthesis becomes firmly implanted in the femur and indeed may be completely embedded therein.

Whilst these femoral implants are useful and provide the patient with an improved quality of life they do not have an infinite life and with time start to fail. This may be due to failure of the prosthesis itself, damage to the bone surrounding the implant or problems with both the prosthesis and the surrounding bone. In general a femoral prosthesis would be expected to have a life of about fifteen years. Whilst this may be acceptable for an older patient, in younger patients it may be necessary to remove and replace the prosthesis at least once during the patient's life. Such procedures are known as revision procedures.

The first stage in any revision procedure is the removal of the failed prosthesis. Although with wear the prosthesis may have loosened within the bone in the sense that it is not held as strongly in position as is required for optimum performance, it can still be difficult to remove. In other situations the prosthesis whilst having "failed" will still be firmly located in place and will be very difficult to remove.

In conventional revision procedures, it is necessary to insert cutting instruments between the periphery of the prosthesis and the bone until the prosthesis and the bone become separated. The act of insertion and/or any subsequent cutting can damage the bone surrounding the prosthesis. A further problem is that excess bone may be removed with the implant. This goes against recommended surgical practice which specifies that only the minimal amount of bone should be removed from the patient. The removal of excess bone is disadvantageous since not only is the size of the replacement prosthesis required to fill the new space in the bone larger, but more seriously, in order for a successful insertion of the replacement prosthesis to be achieved, sufficient bone must be retained in order that the replacement prosthesis may be secured in position. Thus excess bone removal can jeopardise the chances of successfully implanting the replacement prosthesis.

Figure 1:
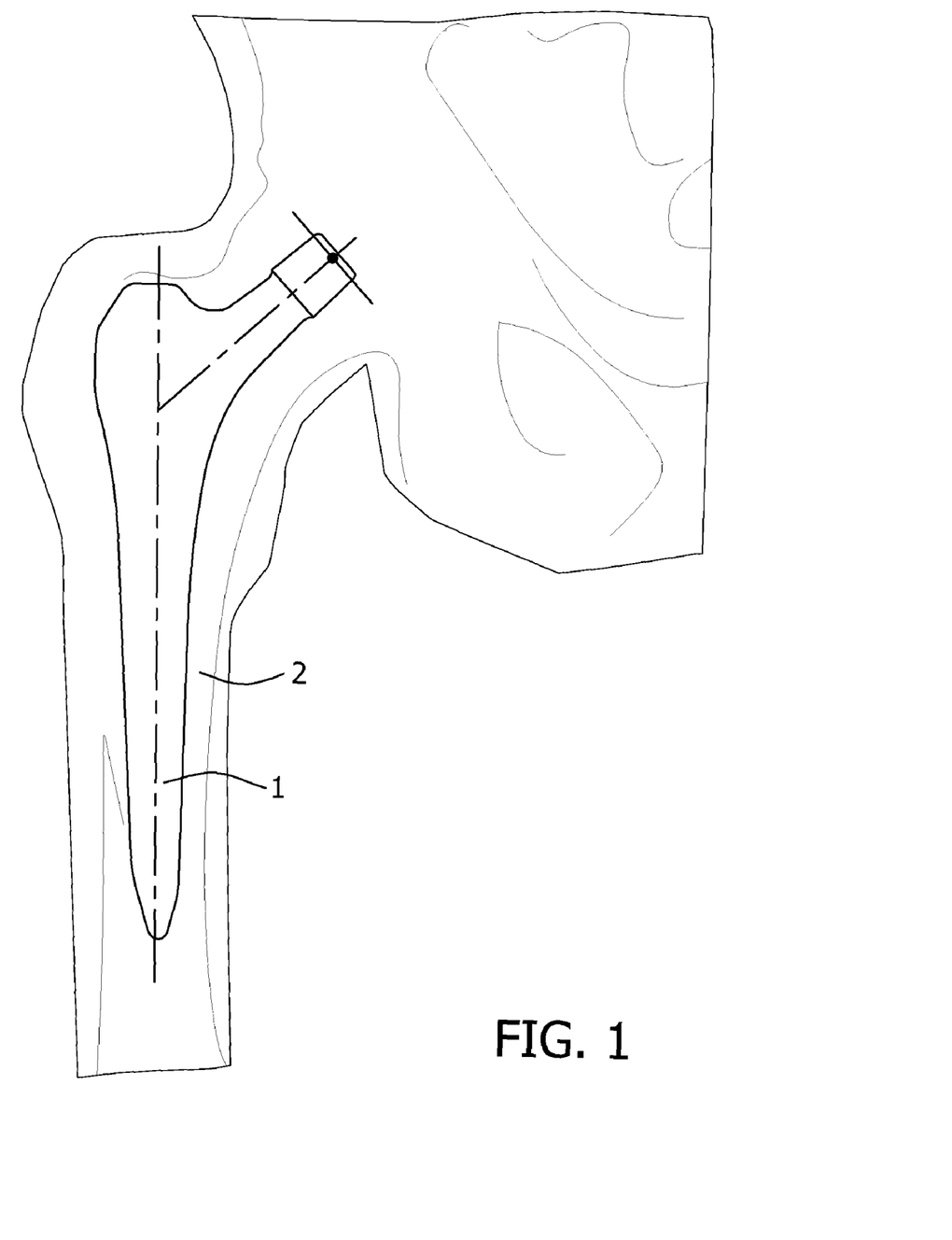
FIG. 1 is a schematic illustration of a femoral stem prosthesis located in a femur.

Whenever it is necessary to remove a prosthesis, difficulties are encountered. However, particular difficulties may be noted where the prosthesis to be removed is a femoral head prosthesis. An example of a femoral head prosthesis in situ in a femur is illustrated in FIG. 1. As can be seen, the stem 1 of the prosthesis extends a substantial distance into the femoral bone 2 and thus it can be difficult to insert the cutting instruments, which are required to loosen the prosthesis, to a sufficient depth. Further, in view of the tapering nature of the prosthesis, it can be difficult to operate any cutting mechanism as the instrument is inserted further into the femur.

A further problem encountered is that as the cutting instruments are inserted between the bone and the prosthesis, debris created by the cutting action, which may include cement and/or bone fragments, may become driven downwardly between the shaft of the prosthesis and the bone where they can form a blockage to further cutting or more seriously they may be impacted into the healthy bone where they may cause damage. In this connection, it will be understood that whilst the debris is generally particulate, with the pressures present, the particles can come together to form a solid mass.

On occasion, in order to remove the prosthesis, it is necessary to cut into the femur at its base so that the formal prosthesis can be driven out of the femur from below.

Similar extreme methods are required to remove other prosthesis particularly these which are implanted into a bone.

In other arrangements a prosthesis may have a flat surface which is placed against the bone or a resected portion thereof. When the prosthesis is cemented in position or where bone in-growth has occurred, removal of the prosthesis, whilst potentially easier than for prosthesis inserted into the bone, the strong bond between the prosthesis and the bone in these arrangements can mean that as the prosthesis is prised from the bone surface, portions of bone come away.

There is therefore a need for an improved tool which will facilitate the removal of a prosthesis, particularly of a femoral head prosthesis, from the bone in which it is integrated.

For the purposes of the present application by "integrated" we mean where the prosthesis is securely attached to the bone whether by cement, adhesives and/or bone in-growth or other means.

Thus according to the present invention there is provided a saw for the removal of a prosthesis which is integrated with a bone, said saw comprising:

a handle; and a blade connected to the handle wherein the distal end of the blade includes a shaped nib;

said shaped nib having teeth, at least some of said teeth being angled to cut as the saw is moved backwardly; said nib additionally including means for allowing the nib to be reversibly deformed such that in use its maximum width can be temporarily reduced.

The handle and the nib may be separate components or may be integrally formed.

In use the saw is inserted between the bone and the prosthesis. The ability of the nib to be deformed such that its maximum width is reduced facilitates the insertion of the saw between the bone and the prosthesis. As sawing action takes place and the prosthesis becomes loosened within the bone, the nib can return to the rest, wider, position. Thus the amount of space taken up by the nib of the saw is minimised at the time of insertion and/or as the saw is advanced further, however, when working an area into which the saw has already been inserted or when moving the saw backwardly, for example, when removing it, it is able to open to the maximum width.

The blade of the saw will generally include a shaft portion which, where present will be located between the nib and the handle. It will be understood that where the prosthesis to be removed is small, it is possible that the nib will comprise the whole of the blade. However, generally the shaft will be present to give the saw the necessary length to reach the end of the prosthesis. The shaft portion will generally be shaped to correspond to the outer shape of at least one edge of the prosthesis against which it is to be used. The shape of the nib region may be similarly shaped. Thus the choice of the shape of the shaft and/or nib of the blade will depend on the shape of the prosthesis to be removed.

Where the prosthesis to be removed is a femoral head prosthesis, the blade will generally be U-shaped in cross-section; this will enable it to be inserted against and in close proximity to the stem of a femoral prosthesis. The size will depend on the prosthesis to be removed. Ideally it will be a close fit around at least a portion of the stem of the prosthesis. The diameter of stems of femoral prostheses is generally from about 8 mm to 18 mm and thus the size of the blade to remove a femoral prosthesis will be of a corresponding size.

Where the prosthesis to be removed is, for example, flat on the bone, the blade will generally be flat.

The length of the blade will depend on the prosthesis to be removed. Where the prosthesis to be removed is the stem of a femoral head prostheses it will be of a similar length to that of conventional stems, namely about 100 mm in length.

The nib may be of any suitable length and may, in one arrangement, comprise up to about a quarter of the length of the blade.

The nib may be of any suitable configuration but it will generally be shaped to reduce the size of the blade. In one arrangement the nib may be shaped such that in appearance it is similar to the underside of a nib for a fountain pen. That is to say, it will slope downwardly from the height of the sides of the shaft, where present, to a point located at or near a point at the distal end.

In general, the edge of the nib will include teeth. These teeth may be of any suitable configuration but will generally cut as the saw is pulled in a backwards direction rather than as it is pushed in a forward direction. In one arrangement, the teeth may cut in both a backward and a forward direction. In one alternative arrangement, the nib may include front teeth which are those closest to the distal end of the blade and which cut in a backwards direction and back teeth which are located further away from the end of the saw than the front teeth and which cut in both a forward and backward direction.

Where a shaft is present, teeth may be present on at least a portion thereof.

One benefit of the teeth cutting as the saw is moved backwardly, i.e. as it is extracted, is that the debris caused by the sawing will be removed with the saw rather than being impacted into the space between the prosthesis and the bone.

The means for allowing the nib to be reversibly deformed during insertion of the saw such that its maximum width is reduced may be of any suitable arrangement. In one arrangement, the nib may have a channel removed from the material of which it is made such that at least a portion of the nib is formed from two tines separated by the channel. The channel means that as the tool is introduced, the tines can move together into the area of the channel thereby reducing the overall width of the nib. In this arrangement, the nib will be formed of material having the necessary properties to allow this to occur. The channel may be substantially straight. However, in one arrangement, the channel may not be straight and may, in one arrangement, have a zig-zag configuration.

The shaft of the blade where present and the nib may be formed of any suitable material. However, they will generally be formed from metal. Suitable metals include stainless steel or high carbon steel.

A striker plate may be provided on the handle at the end remote from the blade. The plate may sit directly on the handle or be integral therewith or, in an alternative arrangement, may be mounted on a stem. In this arrangement, the surgeon can strike the striker plate with a mallet when more force is required to move the saw downwardly than can be provided manually. The striker plate will generally be produced from metal. In one arrangement, the blade and the striker plate may be formed of a single piece of metal. The handle may be formed from the same piece of metal or may be formed from a separate piece of metal or of another material and then positioned connected to the blade by any suitable means.

Where the prosthesis to be removed is a femoral stem prosthesis, the saw of the present invention may include a wing located on the upper end of each side of the blade. The outer edge of each wing will include backward-facing teeth. In use, these wings act to release the sides of the femoral stem prosthesis.

The wings may also be present in other configuration including the flat arrangement.

The blade may be permanently fixed to the handle or may be removable. Thus the blade may be disposable and a number of blades can be replaced on the handle.

The present invention will now be described by way of example with reference to the following drawings in which.

BRIEF DESCRIPTION OF THE DRAWINGS

DETAILED DESCRIPTION OF THE INVENTION

Figure 2:
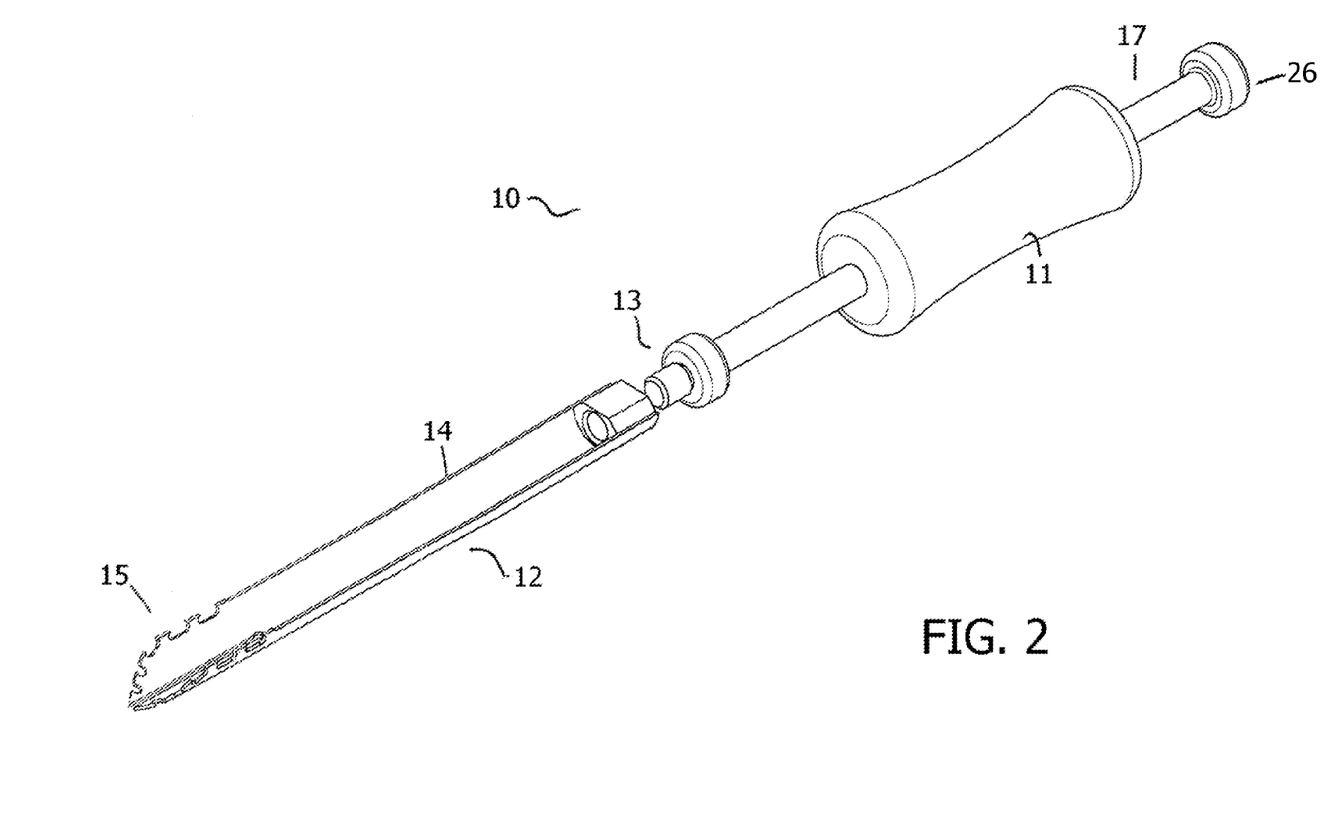
FIG. 2 is a perspective view of one embodiment of the saw of the present invention.

As illustrated in FIG. 2, the saw 10 of the first embodiment comprises a handle 11 and a blade 12. In this arrangement, the blade 12 is removable from the handle and is connected thereto by bolt 13. The blade 12 comprises a shaft 14 and a nib 15. A striker plate 26 is located on a stem 17. The blade 12 may be single use. In this arrangement, the handle may be reusable.

Figure 3:
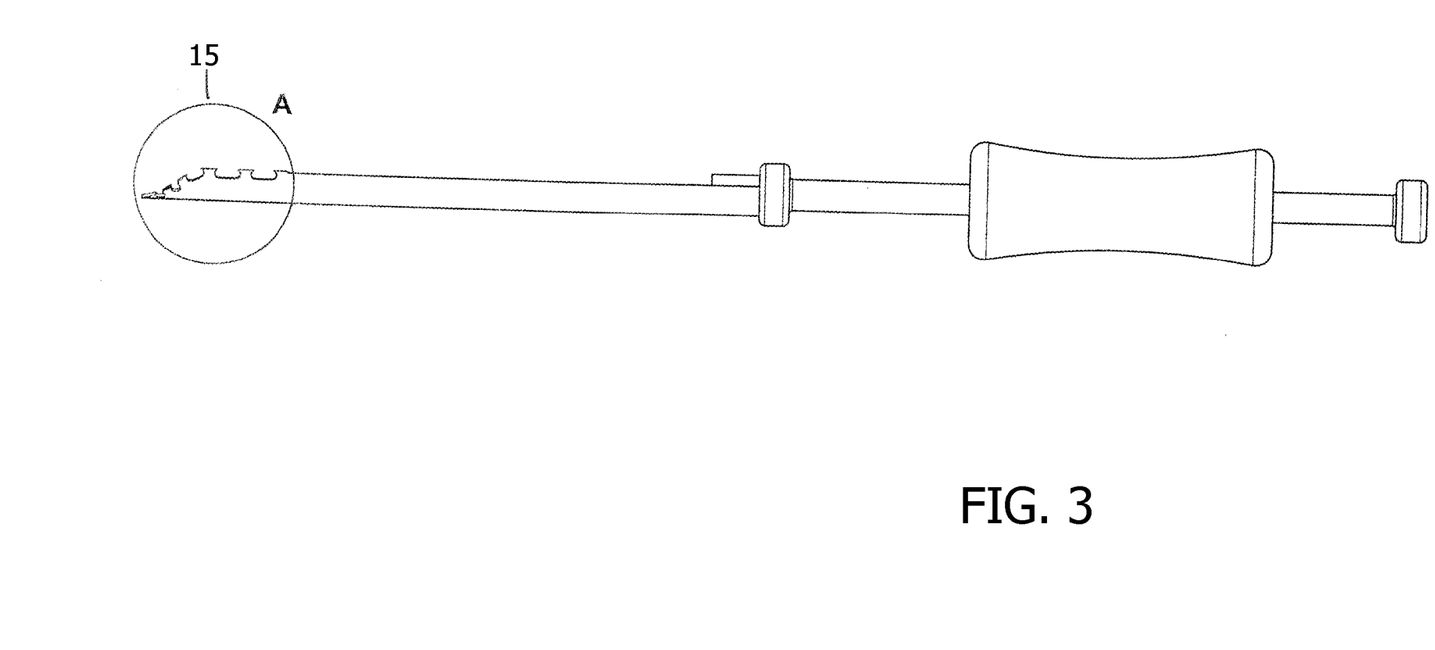
FIG. 3 is a side view of the saw of FIG. 2.
Figure 4:
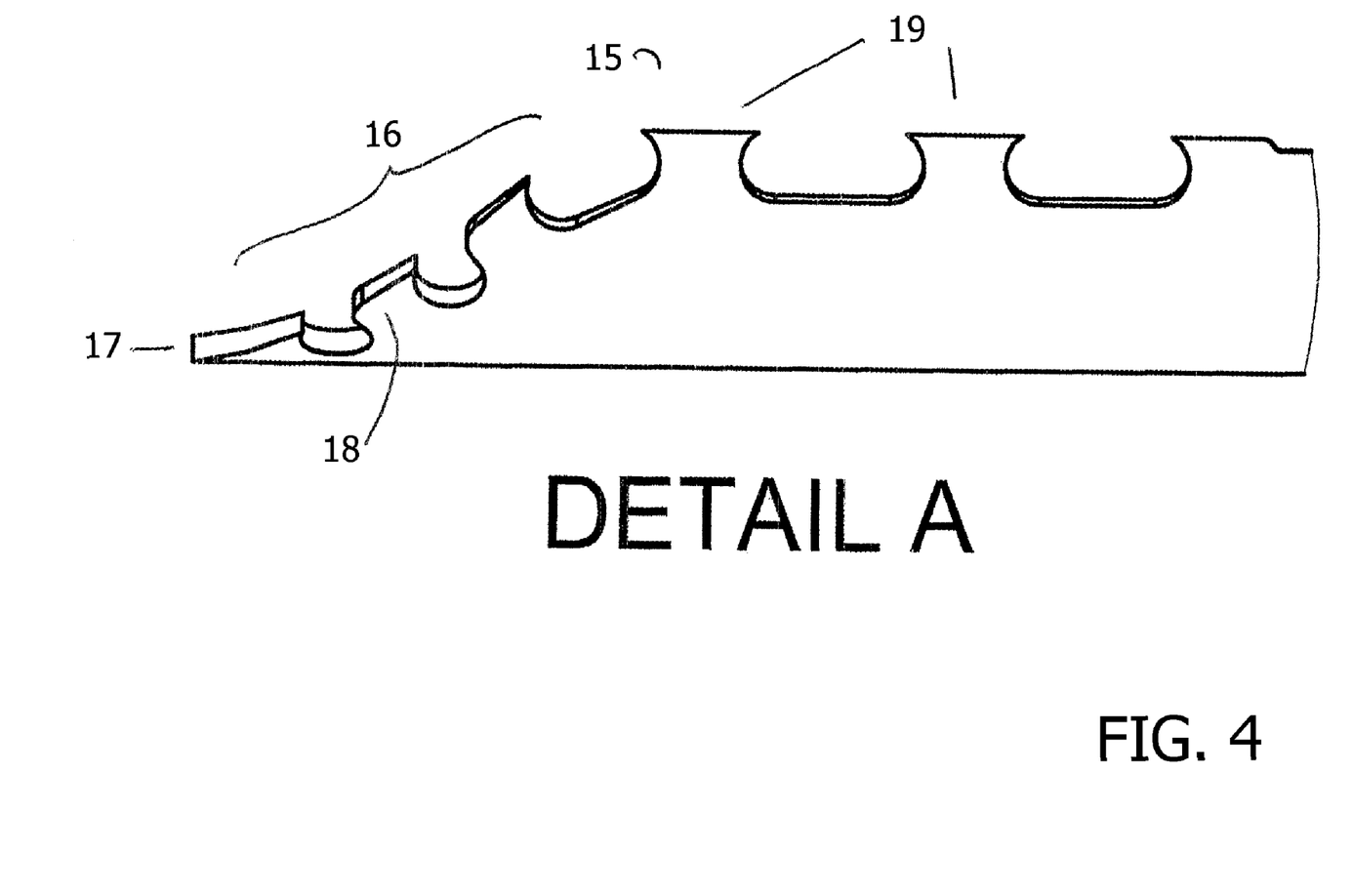
FIG. 4 is a close up of the region A of the saw in FIG. 3.

A side view of the saw 10 is illustrated in FIG. 3. As can be clearly seen, but as illustrated in close-up in FIG. 4, the nib 15 has a sloped side 16 which culminates in a point 17. Front teeth 18 located on the sloped side 16 are shaped to cut as the saw is moved backwardly. Back teeth 19 are provided on the shaft and are shaped to cut in both a forward and a backward direction.

Figure 5:
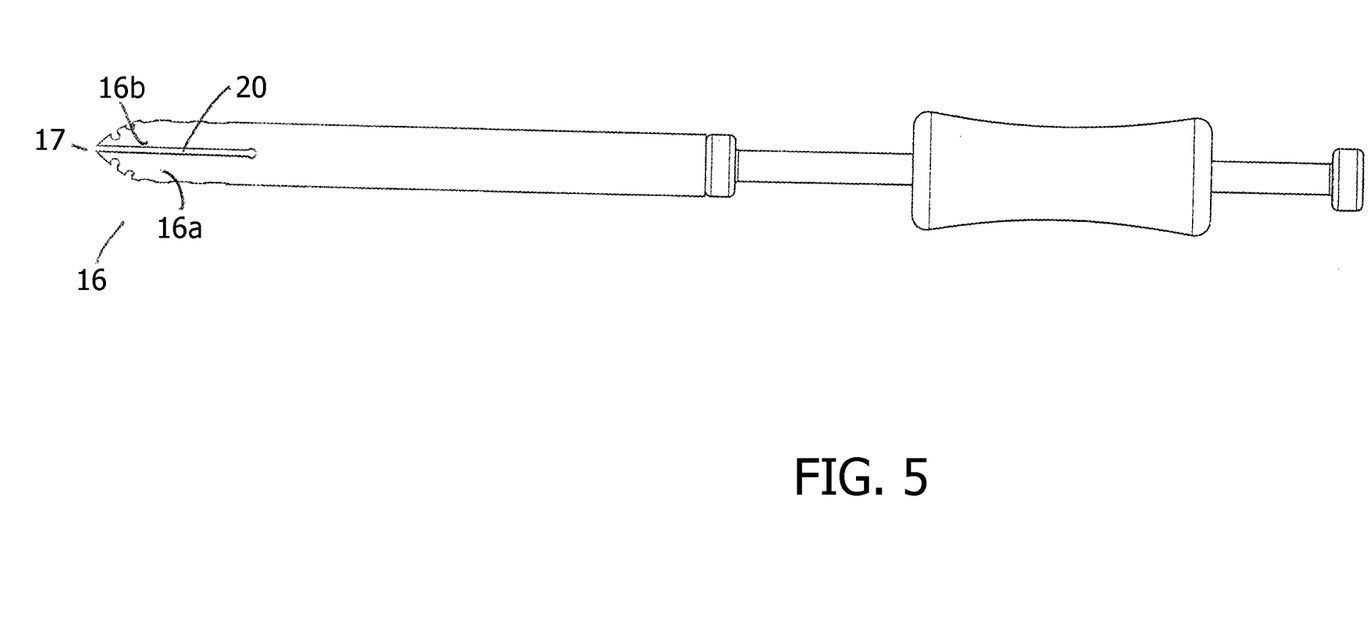
FIG. 5 is a view from below of the saw of FIG. 3.

As illustrated in FIG. 5, a channel 20 is cut from at least the nib region of the blade. This channel 20 continues backwardly from the tip 17. The presence of the channel 20, divides the nib into two tines 16a and 16b. This presence of this channel 20 enables the tines 16a and 16b to move towards each other into the space formed by the channel thereby increasing the width of the nib thereby assisting the insertion. The material from which the blade is formed, allows the tines 16a and 16b to move towards one another and then once the blade is inserted a portion, the move back to the initial position such that the teeth 18 can engage the material they are to cut.

Figure 6:
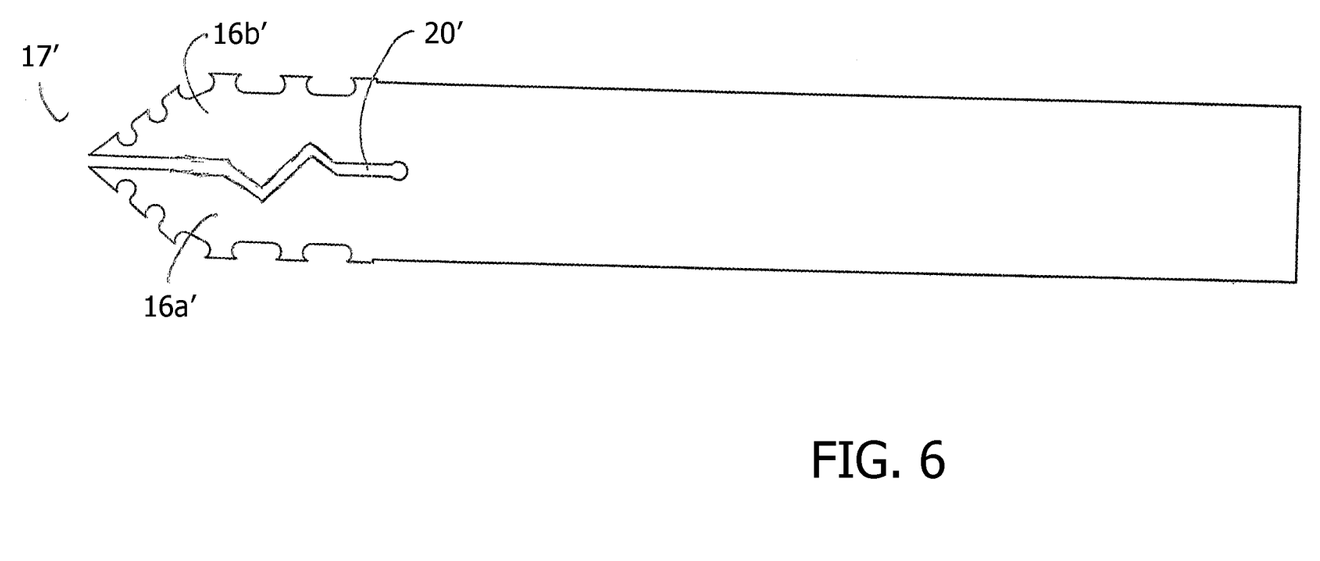
FIG. 6 is a view of the nib region of an alternative nib.

An alternative arrangement for the tip 17' is illustrated in FIG. 6. As in the arrangement of FIG. 5, the channel 20' continues backwardly from the tip 17'. The pressure of the channel 20', divides the nib into the tines 16a' and 16b'. In this arrangement, the channel 20' is not straight but shaped in a zig-zag arrangement.

Figure 7:
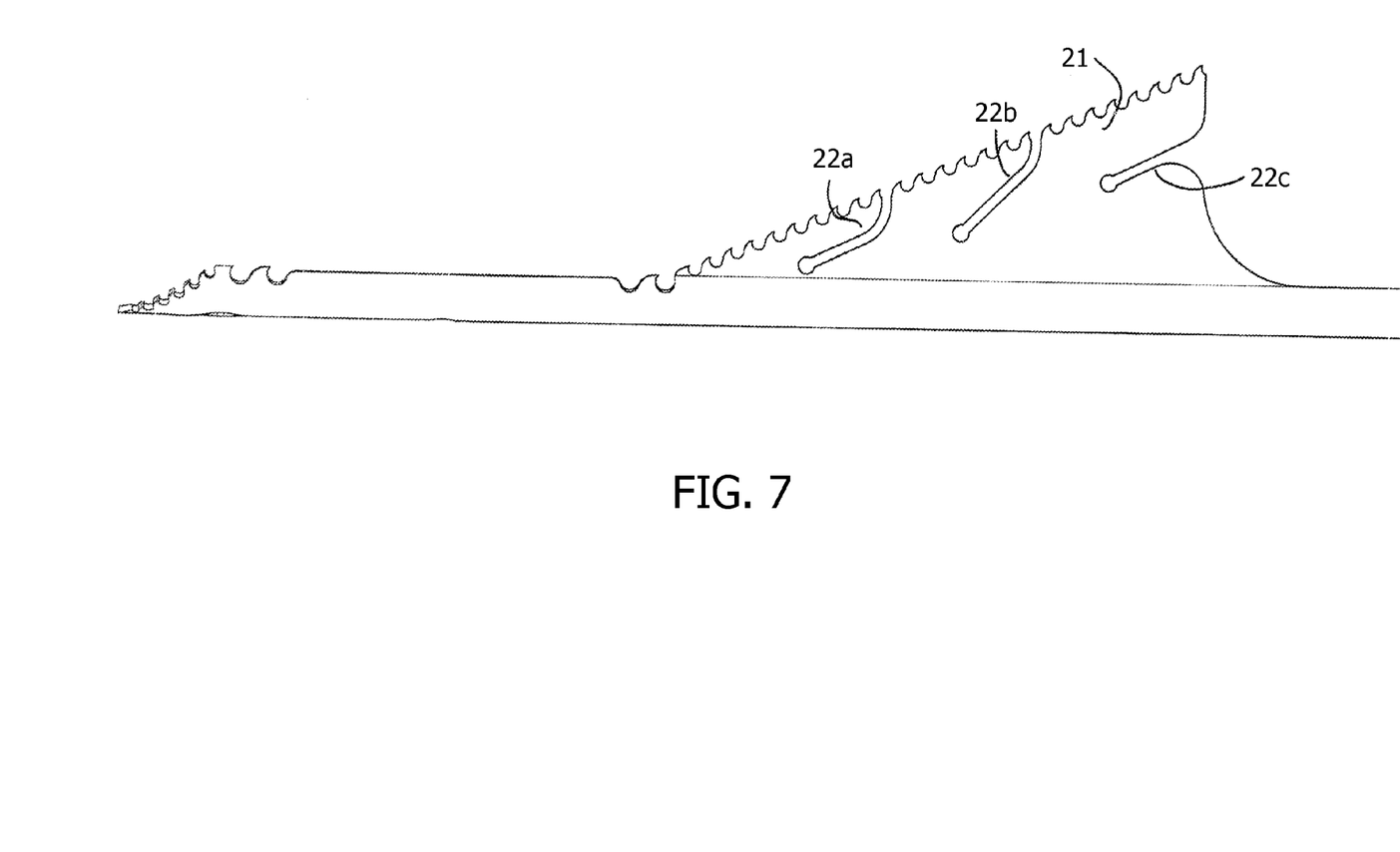
FIG. 7 is a side view of a saw blade of an alternate configuration.
Figure 8:
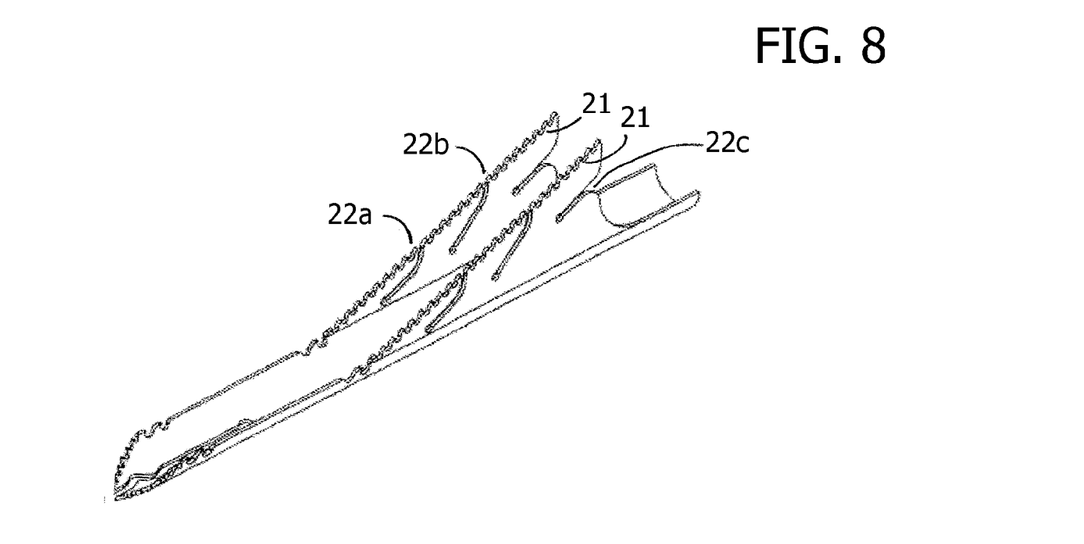
FIG. 8 is a perspective view of the saw blade of FIG. 7.
Figure 9:
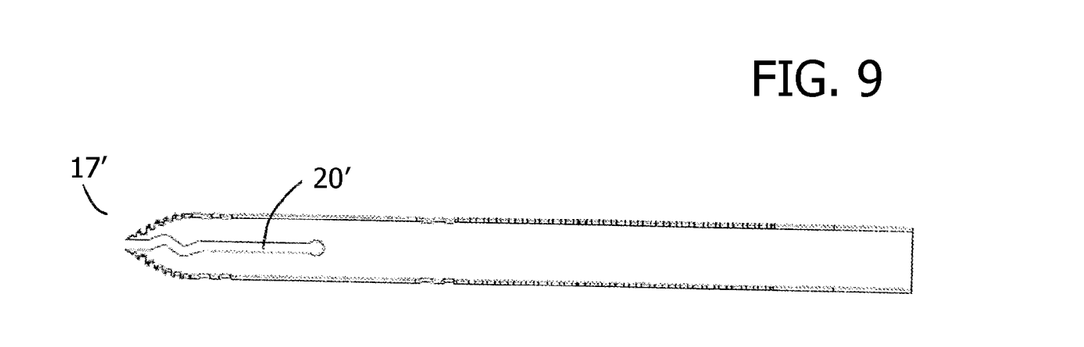
FIG. 9 is a view from above of the saw blade of FIG. 8.

An alternative blade is illustrated in FIG. 7. In this arrangement wings 21 are located on the proximal end of the blade. This edge of the blade is provided with a plurality of backwardly facing teeth. These wings allow the sides of the femoral stem prosthesis to be loosened from the femur. Each wing is provided with channel 22a, 22b and 22c. These will act in the same way as the channel in the nib. A perspective view of the blade is illustrated in FIG. 8 and a view from above in FIG. 9.

Figure 10:
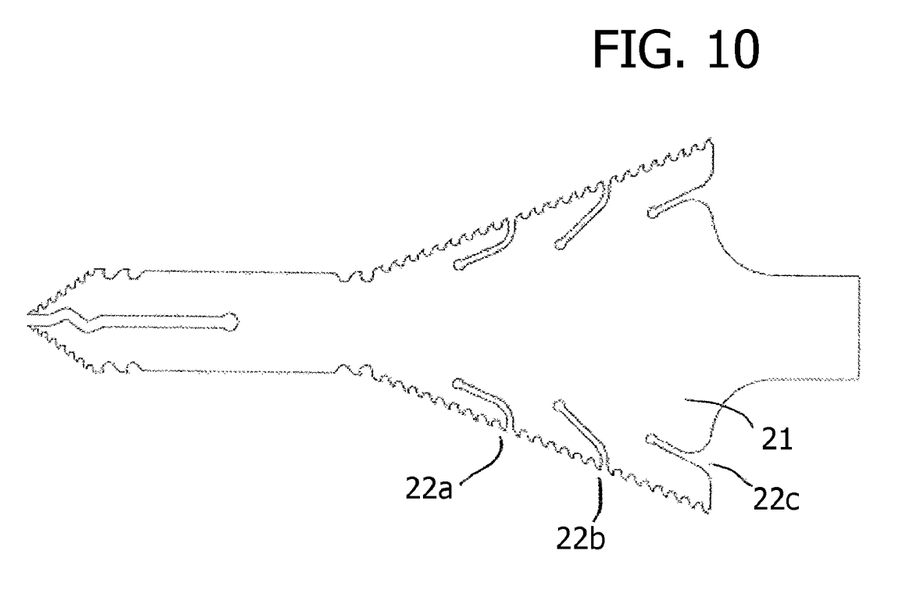
FIG. 10 is a blade of FIG. 7 in a flat configuration.

A blank which can be curved to form the blade of FIG. 7 is illustrated in FIG. 10. This blank can also be used as a flat blade.

Whilst the exemplified saw relates to a saw for removing a femoral stem prosthesis, it will be understood that modifications can be made to provide saws suitable for removing other prosthesis.

What is claimed is:

1. A reciprocating saw for the removal of a prosthesis which is integrated with a bone, said saw comprising:
    a handle; and
    a blade having a longitudinal axis and a transverse axis, the blade being connected to the handle wherein the distal end of the blade includes a shaped nib, the blade being configured to be moved in a forward direction and a backward direction wherein the forward and backward directions are generally along the longitudinal axis of the blade;
    said shaped nib having teeth, at least some of said teeth being angled to cut as the saw is moved in the backward direction and wherein the nib has a channel removed from the material of which it is made such that at least a portion of the nib is formed from two tines separated by the channel and wherein said tines are longer than the teeth.
2. The saw according to claim 1 wherein the blade includes a shaft portion located between the nib and the handle.
3. The saw according to claim 1 wherein the blade is generally U-shaped in cross-section taken along the transverse axis.
4. The saw according to claim 1 wherein the blade is generally flat.
5. The saw according to claim 1 wherein the nib is shaped to reduce the size of the blade.
6. The saw according to claim 5 wherein the nib slopes downwardly to a point.
7. The saw according to claim 1 wherein at least some of said teeth cut only when the blade is moved in the backward direction.
8. The saw according to claim 1 wherein at least some of said teeth cut both when the blade is moved in the backward direction and the forward direction.
9. The saw according to claim 1 wherein the nib includes front teeth which are closest to a distal end of the blade and which cut when the blade is moved in the backward direction and back teeth which are located further away from the distal end of the blade and which cut when the blade is moved in both the forward direction and the backward direction.
10. The saw according to claim 1 additionally including a shaft.
11. The saw according to claim 10 wherein teeth are present on at least a portion of the shaft.
12. The saw according to claim 1 wherein the channel is not straight.
13. The saw according to claim 1 wherein a striker plate is provided on the handle at the end remote from the blade.

* * * * *